United States Patent
He et al.

(10) Patent No.: US 11,154,477 B2
(45) Date of Patent: *Oct. 26, 2021

(54) USE OF ALKANOLAMINE ALKYLAMIDES AS HUMECTANTS

(71) Applicant: Akzo Nobel Chemicals International B.V., Arnhem (NL)

(72) Inventors: Qiwei He, Belle Mead, NJ (US); Hanamanthsa Bevinakatti, Somerset, NJ (US)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/070,366

(22) PCT Filed: Sep. 13, 2016

(86) PCT No.: PCT/EP2016/071591
§ 371 (c)(1),
(2) Date: Jul. 16, 2018

(87) PCT Pub. No.: WO2017/129274
PCT Pub. Date: Aug. 3, 2017

(65) Prior Publication Data
US 2019/0021970 A1 Jan. 24, 2019

Related U.S. Application Data

(60) Provisional application No. 62/289,026, filed on Jan. 29, 2016.

(51) Int. Cl.
| | | |
|---|---|---|
| A61K 8/42 | (2006.01) | |
| A61Q 5/12 | (2006.01) | |
| A61Q 19/00 | (2006.01) | |

(52) U.S. Cl.
CPC .......... *A61K 8/42* (2013.01); *A61Q 5/12* (2013.01); *A61Q 19/00* (2013.01); *A61K 2800/48* (2013.01); *A61K 2800/80* (2013.01)

(58) Field of Classification Search
None
See application file for complete search history.

(56) References Cited

U.S. PATENT DOCUMENTS

| | | | |
|---|---|---|---|
| 4,143,159 A | 3/1979 | Moller et al. | |
| 4,851,434 A | 7/1989 | Deckner | |
| 5,106,838 A * | 4/1992 | Reinhart | A61K 8/37 514/59 |
| 6,395,269 B1 * | 5/2002 | Fuller | A61K 8/046 424/400 |
| 7,666,396 B2 | 2/2010 | Lange et al. | |
| 7,816,310 B2 | 10/2010 | Landa et al. | |
| 8,795,697 B2 | 8/2014 | Brown | |
| 2003/0130636 A1 | 7/2003 | Brock et al. | |
| 2005/0058674 A1 | 3/2005 | Joseph et al. | |
| 2005/0058693 A1 | 3/2005 | Joseph et al. | |
| 2005/0101927 A1 | 3/2005 | Joseph et al. | |
| 2005/0113268 A1 | 5/2005 | Landa et al. | |
| 2005/0113269 A1 | 5/2005 | Landa et al. | |
| 2005/0226839 A1 * | 10/2005 | Huang | A61Q 19/00 424/70.14 |
| 2005/0271595 A1 | 12/2005 | Brown | |
| 2007/0292400 A1 * | 12/2007 | Lipton | A61K 8/982 424/93.7 |
| 2012/0277444 A1 | 11/2012 | Mahadevan et al. | |
| 2016/0289460 A1 * | 10/2016 | Ito | C09D 11/38 |
| 2016/0333209 A1 * | 11/2016 | Shimono | B41M 5/0017 |

FOREIGN PATENT DOCUMENTS

| | | |
|---|---|---|
| CN | 1778287 A | 5/2006 |
| EP | 1 535 607 A1 | 6/2005 |
| EP | 1 455 722 B2 | 12/2011 |
| GB | 1 554 251 A | 10/1979 |
| GB | 1 589 224 A | 5/1981 |
| JP | 2000-327551 A | 11/2000 |
| JP | 2007-137786 A | 6/2007 |
| JP | 5334511 B2 | 8/2013 |
| WO | 2004/022115 A1 | 3/2004 |
| WO | 2004/022116 A1 | 3/2004 |
| WO | 2004/022117 A1 | 3/2004 |
| WO | WO2015125368 * | 8/2015 |
| WO | 2017/129272 A1 | 8/2017 |
| WO | 2017/129273 A1 | 8/2017 |

OTHER PUBLICATIONS

JP2000-327551 Machine Translation, Nov. 28, 2000 (Year: 2000).*
JP 2000327551, Machine Translation, pub date: 2000 (Year: 2000).*
Brenntag Canada, Titanium Dioxide MSDS, Feb. 22, 2016 (Year: 2016).*
Humectant, Merriam Webster Dictionary, https://www.merriam-webster.com/dictionary/humectant, retrieved online on Jun. 29, 2020 (Year: 2020).*
Notification of Transmittal of the International Search Report and the Written Opinion of the International Searching Authority, or the Declaration from the International Bureau of WIPO for International Application No. PCT/EP2016/071591 dated Nov. 9, 2016.

(Continued)

*Primary Examiner* — Jennifer A Berrios
(74) *Attorney, Agent, or Firm* — Norris McLaughlin, P.A.

(57) ABSTRACT

The disclosure provides personal care compositions that comprise a compound of formula (I) wherein n is an integer from 2 to 5, $R^1$ is independently H or $C_1$-$C_3$ alkyl and $R^2$ is an unsubstituted linear or branched $C_1$-$C_6$ alkyl and a cosmetically acceptable vehicle. In particular, the compound of formula (I) is diglycolamine acetamide The composition may be used to moisturise skin or hair.

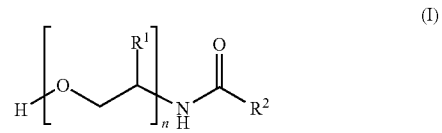

14 Claims, 1 Drawing Sheet

(56) References Cited

OTHER PUBLICATIONS

Krakowiak et al., "A New Building Block Method to Synthesize Symmertrical and Asymmetrical Per-N-alkyl-Substituted Polyaza-Crown Compounds," vol. 54, No. 17, 1989, pp. 4061-4067, XP055308514.
Anonymous: Technical Bulletin, Amides From Diglycolamine® Agent Diglycolamine® Agent [CAS 929-06-06], Jan. 1, 2007, XP055308615.
Lange et al., "The homologs of monoethanolamine," Bulletin de la Societe Chimique de France (1951) 340-1, Abstract only.
Khanina et al., "Oxyethylation of amides of aliphatic low molecular acids as an experimental approach to obtaining new nontoxic cryoprotectants," Problemy Kriobiologii (1994), (3), 30-5, Institut Problem Kriobiologii i Kriomeditsiny NAN Ukrainy, Abstract only.
Ratchford, "N-Hydroxyalkyl amides of lactic acid. Preparation and properties," Industrial and Engineering Chemistry (1950), 42, 1565-7, Abstract only.
"Cosmetics Q&A: Why are cosmetics not FDA-approved?" p. 1, obtained from website fda.gov on Nov. 22, 2019.
"Color Additives Permitted for Use in Cosmetics," pp. 1-5, obtained from website fda.gov on Nov. 22, 2019.
"Color Additives and Cosmetics: Fact Sheet," pp. 1-5, obtained from website fda.gov on Nov. 22, 2019.
"What's the Difference Between an Emollient and a Humectant?" pp. 1-4, obtained from the website orogold.cosmetics.com on Sep. 23, 2019.

\* cited by examiner

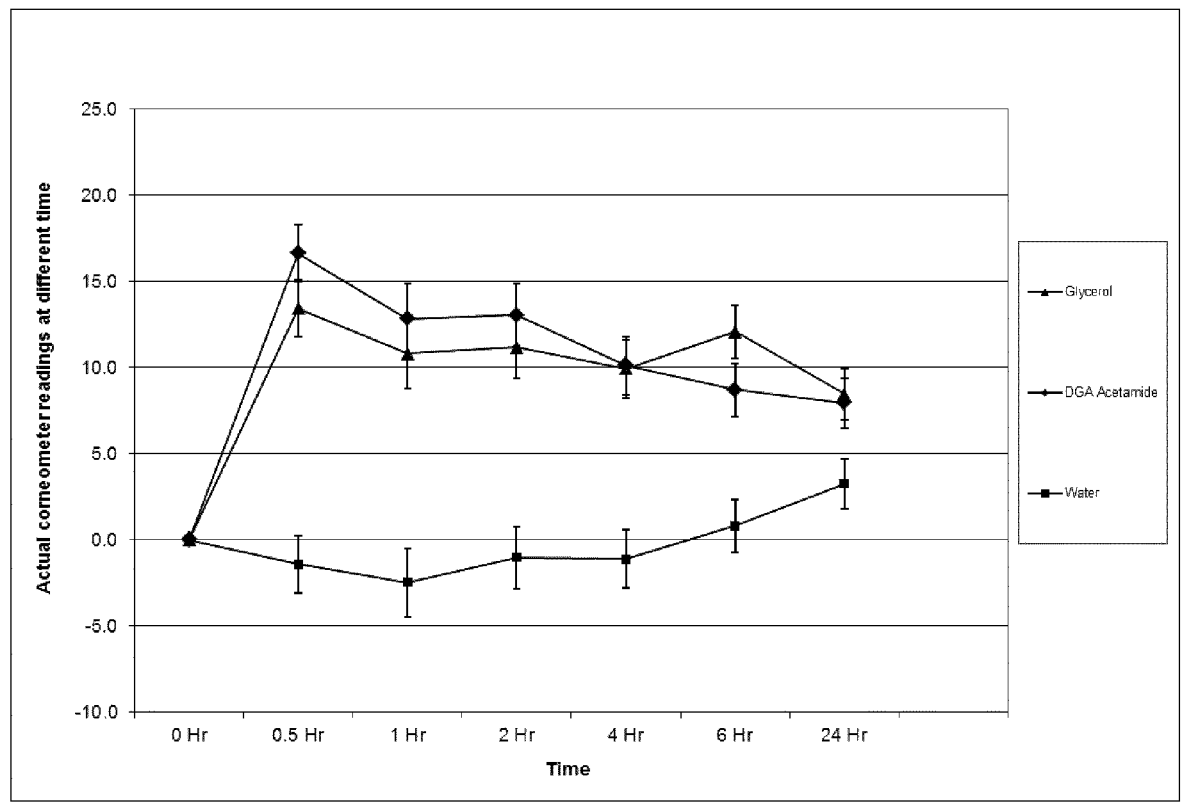

USE OF ALKANOLAMINE ALKYLAMIDES AS HUMECTANTS

This application is a national stage filing under 35 U.S.C. § 371 of PCT/EP2016/071591, filed Sep. 13, 2016, which claims priority to U.S. Provisional Patent Application No. 62/289,026, filed Jan. 29, 2016, the contents of which are each incorporated herein by reference in their entireties.

BACKGROUND OF THE INVENTION

Field of the Invention

The disclosure generally provides personal care compositions that improve moisturization.

Description of Related Art

A significant segment of the population uses products to moisturize their skin and/or hair, and such segment continues to grow at a substantial rate. When trying to provide or increase moisturizing efficacy, many of the moisturizing products currently on the market also leave a heavy, greasy feel that consumers find undesirable. Thus there is a need in the art for a long-lasting moisturizer that does not have qualities undesirable to the user.

SUMMARY OF THE INVENTION

We recognized a need for personal care compositions with improved moisturizing efficacy. Several humectants have been known and used in personal care compositions. Many of the known humectants, including the most widely used (glycerol), are sticky, tacky, or greasy when applied on the skin. In a broad aspect, the disclosure provides personal care formulations that have an improved, smooth feel on the skin that is desirable by the consumers. Specifically, the personal care formulations of the disclosure exhibit less waxiness, greasiness, stickiness, tackiness, or heavy feeling, and, for example, are easy to spread on the skin. Furthermore, the personal care formulations of the disclosure have improved moisturization efficacy on skin and/or hair. In some embodiments the personal care formulations of the disclosure also can provide long term moisturization, for example, up to 30 hours after a single application.

Thus, one aspect of the disclosure provides personal care formulations comprising a compound of formula (I)

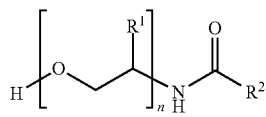

(I)

wherein
n is an integer from 2 to 5;
$R^1$ is independently H or $C_1$-$C_3$ alkyl; and
$R^2$ is an unsubstituted linear or branched $C_1$-$C_6$ alkyl, and a cosmetically acceptable vehicle.

The personal care formulations of the disclosure provide moisturization of hair and/or skin by retaining water.

In another aspect, the disclosure provides a kit comprising a container (e.g., a tube or jar) containing a personal care formulation according to the disclosure and instructions for application of the formulation to the skin or hair for enhancing moisturization of the skin or hair, wherein the instructions are printed on the container, on the packaging of the container, or on a document included with the container as part of the kit.

In another aspect, the disclosure provides a method of moisturizing skin or hair, the method comprising applying an effective moisturizing amount of a personal care formulation of the disclosure to the skin or hair, respectively.

In another aspect, the disclosure provides for the use of a compound of formula (I) above as a humectant in a personal care formulation.

BRIEF DESCRIPTION OF DRAWING

FIG. 1 provides Corneometer values for gel formulations comprising each of DGA acetamide, glycerol and water over various time periods, as measured by the procedures of Example 3.

DETAILED DESCRIPTION OF THE INVENTION

Before the disclosed materials and methods are described, it is to be understood that the aspects described herein are not limited to specific embodiments, or configurations, and as such can, of course, vary. It is also to be understood that the terminology used herein is for the purpose of describing particular aspects only and, unless specifically defined herein, is not intended to be limiting.

In view of the present disclosure, the active materials and methods described herein can be configured by the person of ordinary skill in the art to meet the desired need. In general, the disclosed materials provide improvements in personal care formulations, particularly in the skin care and hair care formulations. For example, in certain aspects, the personal care formulations of the disclosure have improved moisturization efficacy on skin and/or hair. In addition, in some embodiments the personal care formulations of the disclosure can provide long term moisturization; for example, up to 30 hours after a single application.

Several humectants have been known and used in personal care formulations. The most widely used humectant, glycerol, is sticky, tacky, and greasy when applied on the skin. In contrast, the personal care formulations of the disclosure have improved feel on the skin. Specifically, the disclosed formulations exhibit diminished waxiness, greasiness, stickiness, tackiness, or heavy feeling, and are easy to spread on the skin.

Personal care formulations of the disclosure comprise a compound of formula (I)

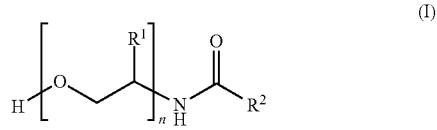

(I)

wherein
n is an integer from 2 to 5,
$R^1$ is independently H or $C_1$-$C_3$ alkyl, and
$R^2$ is an unsubstituted linear or branched $C_1$-$C_6$ alkyl: and a cosmetically acceptable vehicle.

In certain embodiments, personal care formulations comprise the compound of formula (I) wherein n is an integer from 2 to 4. In other embodiments, personal care formulations comprise the compound of formula (I) wherein n is selected from 2 or 3. In one embodiment, personal care formulations comprise the compound of formula (I) wherein n is 2. In another embodiment, personal care formulations comprise the compound of formula (I) wherein n is 3.

In one embodiment, personal care formulations comprise the compound of formula (I) wherein $R^1$ is independently selected from H, methyl, and ethyl. In another embodiment, personal care formulations comprise the compound of formula (I) wherein $R^1$ is independently selected from H and methyl. In certain embodiments, personal care formulations comprise the compound of formula (I) wherein $R^1$ is independently H. In other certain embodiments, personal care formulations comprise the compound of formula (I) wherein $R^1$ is independently methyl.

In certain embodiments, personal care formulations comprise the compound of formula (I) according to any preceding embodiment and wherein $R^2$ is unsubstituted linear or branched $C_1$-$C_4$ alkyl. In certain embodiments, personal care formulations comprise the compound of formula (I) according to any preceding embodiment and wherein $R^2$ is selected from methyl and ethyl. In certain embodiments, personal care formulations comprise the compound of formula (I) according to any preceding embodiment and wherein $R^2$ is methyl.

An example of a particularly useful compound of formula (I) is:

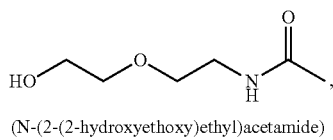

(N-(2-(2-hydroxyethoxy)ethyl)acetamide)

also referred to as N-acetyl diglycolamine, N-acetyl DGA, diglycolamine acetamide, or DGA Acetamide.

Pure DGA Acetamide can also be prepared by the methods published in Krakowiak et al., "A New Building Block Method To Synthesize Symmetrical and Asymmetrical Per-N-alkyl-Substituted Polyaza-Crown Compounds," *J. Org. Chem.*, 54(17): 4061-4067 (1989), incorporated herein by reference in its entirety.

The compound of formula (I) acts as a humectant capable of providing moisturization by, for example, retaining water. Thus, in some embodiments, the compound (I) is present in an amount sufficient to provide an increase in moisturization of skin or hair with which it comes into contact.

In certain embodiments, the compound of formula (I) is present in about 0.5% to about 15% by weight of the personal care formulations. In other embodiments, the compound of formula (I) is present in about 0.5 wt % to about 14 wt %, or about 0.5 wt % to about 13 wt %, or about 0.5 wt % to about 12 wt %, or about 0.5 wt % to about 11 wt %, or about 0.5 wt % to about 10 wt %, or about 0.5 wt % to about 9 wt %, or about 0.5 wt % to about 8 wt %, or about 0.5 wt % to about 7 wt %, or about 0.5 wt % to about 6 wt %, or about 1 wt % to about 15.0 wt %, about 1 wt % to about 14 wt %, or about 1 wt % to about 13 wt %, or about 1 wt % to about 12 wt %, or about 1 wt % to about 11 wt %, or about 1 wt % to about 10 wt %, or about 1 wt % to about 9 wt %, or about 1 wt % to about 8 wt %, or about 1 wt % to about 7 wt %, or about 1 wt % to about 6 wt %, or about 2 wt % to about 15 wt %, about 2 wt % to about 14 wt %, or about 2 wt % to about 13 wt %, or about 2 wt % to about 12 wt %, or about 2 wt % to about 11 wt %, or about 2 wt % to about 10 wt %, or about 2 wt % to about 9 wt %, or about 2 wt % to about 8 wt %, or about 2 wt % to about 7 wt %, or about 2 wt % to about 6 wt %, or about 2 wt % to about 5 wt %, or about 3 wt % to about 15 wt %, about 3 wt % to about 14 wt %, or about 3 wt % to about 13 wt %, or about 3 wt % to about 12 wt %, or about 3 wt % to about 11 wt %, or about 3 wt % to about 10 wt %, or about 3 wt % to about 9 wt %, or about 3 wt % to about 8 wt %, or about 3 wt % to about 7 wt %, or about 3 wt % to about 6 wt %, or about 3 wt % to about 5 wt %, or about 4 wt % to about 15 wt %, about 4 wt % to about 14 wt %, or about 4 wt % to about 13 wt %, or about 4 wt % to about 12 wt %, or about 4 wt % to about 11 wt %, or about 4 wt % to about 10 wt %, or about 4 wt % to about 9 wt %, or about 4 wt % to about 8 wt %, or about 4 wt % to about 7 wt %, or about 4 wt % to about 6 wt %, or about 4 wt % to about 5 wt %, or about 4.5 wt % to about 6.5 wt %, or about 4.5 wt % to about 6 wt %, or about 4.5 wt % to about 5.5 wt %, or about 4.5 wt % to about 5 wt %, or about 4.5 wt %, or about 5 wt % to about 15 wt %, about 5 wt % to about 14 wt %, or about 5 wt % to about 13 wt %, or about 5 wt % to about 12 wt %, or about 5 wt % to about 11 wt %, or about 5 wt % to about 10 wt %, or about 5 wt % to about 9 wt %, or about 5 wt % to about 8 wt %, or about 5 wt % to about 7 wt %, or about 5 wt % to about 6 wt %, or about 5 wt %, or about 5.5 wt %, or about 6 wt %, of the personal care formulations. In certain embodiments, the compound of formula (I) is present in about 4.5% to about 5.5% by weight of the personal care formulation. In some other embodiments, the compound of formula (I) is present in about 4.8% to about 5.2% by weight of the personal care formulation. In some other embodiments, the compound of formula (I) is present in about 5 to about 10% by weight of the personal care formulation.

The personal care formulations of the disclosure also include a cosmetically acceptable vehicle. While the vehicle for personal care formulations can comprise a relatively simple solvent or dispersant such as water, such vehicles can also vary greatly depending upon the type of composition (e.g., skin care or hair care) and the functionality and properties desired. For example, the cosmetically acceptable vehicle may be selected to be more conducive to topical application, including one that will form a film or layer on the skin to which the composition is applied so as to localize the application and provide some resistance to washing off by immersion in water or by perspiration. The vehicles can be creams, lotions, gels, serums, emulsions, or other liquids and can include additional ingredients such as thickening agents (such as gums) or hydrophilic colloids. The cosmetically acceptable vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant. Suitable cosmetically acceptable vehicles and other components are well known to those skilled in the cosmetic formulation art and can be found, for example in McCutcheon's 2015 Emulsifiers and Detergents: North American Edition by Michael Allured, MC Publishing Co., 2015 edition (Mar. 2, 2015), and in McCutcheon's 2015 Functional Materials: North American Edition by Michael Allured, MC Publishing Co., 2015 edition (Mar. 2, 2015), both of which are incorporated by reference herein.

Without limitation, the personal care formulations may comprise one or more ingredients selected from thickeners, surfactants, emulsifiers, suspending agents, pH adjusters and neutralizers, additional humectants, emollients, oils, waxes, solvents, chelating agents, silicones, preservatives, fragrances, dyes, pigments, conditioners, polymers, exfoliants, film formers, propellants, hair fixatives and colorants, and any combination thereof. The compound of formula (I) of the present disclosure is compatible with most other components used in conventional personal care formulations. For example, cosmetic formulations may also contain one or more other components such as vitamins, antioxidants, botanical extracts, styling agents, antiperspirant active ingredients, anti-acne agents, anti-dandruff actives, UV filters, sunscreen actives, tanning accelerators, and other active ingredients.

The CTFA Cosmetic Ingredient Handbook, Seventh Edition, 1997 and the Eighth Edition, 2000, which is incorporated by reference herein in their entirety, describe a wide variety of cosmetic and pharmaceutical ingredients commonly used in skin care compositions that are suitable for use in the compositions of the present disclosure. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, depilatory compounds, drug astringents, external analgesics, film formers, fragrance components, opacifying agents, pH adjusters (such as lactic acid, citric acid, and the like), plasticizers, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, SPF boosters, insect repellants, waterproofing agents, and viscosity increasing agents (aqueous and non-aqueous).

The personal care formulations of the disclosure may include one or more thickening agents. The formulations of the present invention may comprise from about 0.01% to about 10% by weight, from about 0.05% to about 1% by weight, from about 0.1% to about 0.5% by weight, or, alternatively, from about 0.1% to about 0.25% by weight, of a thickening agent or a mixture of thickening agents when present. Suitable classes of thickening agents include but are not limited to carboxylic acid polymers, polyacrylamide polymers, sulfonated polymers, copolymers thereof, hydrophobically modified derivatives thereof, and mixtures thereof. Suitable thickening agents include carboxylic acid polymers such as the carbomers (e.g., the CARBOPOL® 900 series such as CARBOPOL® 940, CARBOPOL® 954 and Carbopol ETD 2050), and Ultrez 10 and Ultrez 30. Other suitable carboxylic acid polymeric agents include copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-30 alkyl acrylate crosspolymers and are commercially available as CARBOPOL® 1342, CARBOPOL® 1382, Ultrez 20, Ultrez 21, PEMULEN TR-1, and PEMULEN TR-2.

The personal care formulations of the disclosure may include one or more surfactants. The compositions of the present invention may comprise from about 0.01% to about 15% by weight, from about 0.05% to about 5% by weight, from about 0.05% to about 1% by weight, from about 0.1% to about 0.5% by weight, or, alternatively, from about 0.1% to about 0.25% by weight, of a surfactant or a mixture of surfactants. The exact surfactant or surfactant mixture chosen will depend upon the pH of the composition and the other components present. Suitable surfactants include anionic, nonionic, cationic, amphoteric, or zwitterionic surfactants. The term surfactant also includes salts of fatty acids, which are typically referred to as soaps. Suitable anionic surfactants include, but are not limited to, soaps or salts of fatty acids, alkyl sulfates, alkyl ether sulfates, alpha-olefin sulfonates, alkyl aryl sulfonates, sarcosinates, alkyl glucose esters or their alkoxylates, sodium lauryl sulfate, ammonium lauryl sulfate, triethanolamine lauryl sulfate, sodium laureth sulfate, isethionates, and triethanolamine stearate. Nonionic surfactants include, but are not limited to, methyl glucose stearates or their ethoxylates, alkyl polyglucosides, and glycerol monostearate, fatty acid alkanol amides, alkyl aryl polyglycol ether, polyglycol ethers and in particular cocoyl diethanolamide, nonoxynol-7 and octoxynol-9. Exemplary cationic surfactants include, but are not limited to, mono- and di-dimethyl ammonium salts, benzalkonium chlorides, di-steary-di-methyl ammonium salts, alkyl trimethyl ammonium salts, quaternized amides of ethylene diamine, alkyl pyridinium salts, cetrimonium chloride, stearalkonium chloride and cetyl pyridinium chloride; and amphoterics including alkyl β-aminopropionates, betaines, alkyl imidazolines, cocamidopropyl betaine and caproam phocarboxy propionate.

The personal care formulations of the disclosure may include one or more emulsifiers. The formulations of the present invention may comprise from about 0.01% to about 10% by weight, from about 0.05% to about 5% by weight, from about 0.05% to about 1% by weight, from about 0.1% to about 0.5% by weight, or, alternatively, from about 0.1% to about 0.25% by weight, of an emulsifier or a mixture of emulsifiers. Exemplary emulsifiers include, but are not limited to, polyoxyethylene oleyl ether, PEG-40 stearate, ceteareth-12, Eumulgin B-1 (Henkel), ceteareth-20, Eumulgin B-2 (Henkel), ceteareth-30, Lanette (Henkel), glyceryl stearate Cutina GMS (Henkel), PEG-100 stearate, methyl myristate, isopropyl myristate, Arlacel 165, glyceryl stearate, PEG-100 stearate, steareth-2 and steareth-20, dimethicone copolyol, Polysorbate 20 (Tween 20), Polysorbate 40 (Tween 40), Polysorbate 60 (Tween 60), Polysorbate 80 (Tween 80), lauramide DEA, cocamide DEA, and cocamide MEA, Phospholipid PTC, alginate, carrageenan, Glucate DO, methylcellulose, polyvinyl alcohol, Cocamidopropyl phosphatidyl PG-dimonium chloride, stearic acid, magnesium stearate, milk amino acids, triethanolamine, and magnesium aluminum silicate.

The personal care formulations of the disclosure may also include one or more preservatives. The formulations of the present invention may comprise from about 0.01% to about 10% by weight, from about 0.05% to about 5% by weight, from about 0.05% to about 1% by weight, from about 0.1% to about 0.5% by weight, or, alternatively, from about 0.1% to about 0.25% by weight, of a preservative or a mixture of preservatives. Exemplary preservatives suitable for use in the present invention may include, but are not limited to, 5-chloro-2-methyl-1,2-thiazol-3-one, 2-methyl-1,2-thiazol-3-one, 1,3-dimethylol-5,5-dimethylhydantoin, 3-iodo-2-propynyl butyl carbamate, KATHON™ CG and GLYDANT™ PLUS™, and parabens such as methylparaben and propylparaben. Additional preservatives may also be used if desired and include well known preservative compositions such as benzyl alcohol, phenyl ethyl alcohol and benzoic acid, diazolydinyl, urea, and chlorphenesin, among others.

The personal care formulations of the disclosure may also include one or more emollients. An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil, grape seed oil, sweet almond oil, and peanut oil. Preferably, the emollient is a cocoglyceride, which is a mixture of mono, di- and triglycerides of cocoa oil, sold under the trade name of Myritol 331 from Henkel KGaA, or Dicaprylyl Ether available under the trade name Cetiol OE from Henkel KGaA or a 012-015 Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of (C12-C15) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semisolid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

Non-limiting examples of film forming polymers suitable for use in formulations of the present invention include but are not limited to: from Akzo Nobel Surface Chemistry LLC, Bridgewater N.J., AMPHOMER and AMPHOMER LV-71 polymers (octylacrylamide/acrylates/butylaminoethyl methacrylate compolymer), AMPHOMER HC polymer (acrylates/octylacrylamide copolymer) BALANCE 0/55, BALANCE CR and DERMACRYL AQF polymers (acrylates copolymer), BALANCE 47 polymer (octylacrylamide/butylaminoethyl methacrylate copolymer), RESYN 28-2930 polymer (VA/crotonates/vinyl neodecanoate copolymer), RESYN 28-1310 polymer (VA/Crotonates copolymer), FLEXAN polymers (sodium polystyrene sulfonate), DynamX polymer (polyurethane-14 (and) AMP-Acrylates copolymer), RESYN XP polymer (acrylates/octylacrylamide copolymer), STRUCTURE 2001 (acrylates/steareth-20 itaconate copolymer) and STRUCTURE 3001 (acrylates/ceteth-20 itaconate copolymer); from ISP, OMNIREZ-2000 (PVM/MA half ethyl ester copolymer), GANEX P-904 (butylated PVP), GANEX V-216 (PVP/hexadecene copolymer) GANEX V-220 (PVP/eicosene copolymer), GANEX WP-660 (tricontanyl PVP), GANTREZ A425 (butyl ester of PVM/MA copolymer), GANTREZ AN-119 PVM/MA copolymer, GANTREZ ES 225 (ethyl ester of PVM/MA copolymer), GANTREZ ES425 (butyl ester of PVM/MA copolymer), GAFFIX VC-713 (vinyl caprolactam/PVP/dimethylaminoethyl methacrylate copolymer), GAFQUAT 755 (polyquaternium-11), GAFQUAT HS-100 (polyquaternium-28) AQUAFLEX XL-30 (Polyimide-1), AQUAFLEX SF-40 (PVPNinylcaprolactum/DMAPA Acrylates Copolymer), AQUAFLEX FX-64 (Isobutylene/Ethylmaleimide/Hydroxyethylmaleimide Copolymer), ALLIANZ LT-120 (Acrylates/C1-2 Succinates/Hydroxyacrylates Copolymer), STYLEZE CC-10 (PVP/DMAPA Acrylates Copolymer), STYLEZE 2000 (VP/Acrylates/Lauryl Methacrylate Copolymer), STYLEZE W-20 (Polyquaternium-55), Copolymer Series (PVP/Dimethylaminoethylmethacrylate Copolymer), ADVANTAGE S and ADVANTAGE LCA (VinylcaprolactamNP/Dimethylaminoethyl Methacrylate Copolymer), ADVANTAGE PLUS (VA/Butyl Maleate/Isobornyl Acrylate Copolymer); from BASF, ULTRAHOLD STRONG (acrylic acid/ethyl acrylate/t-butyl acrylamide), LUVIMER 100P (t-butyl acrylate/ethyl acrylate/methacrylic acid), LUVIMER 36D (ethyl acrylate/t-butyl acrylate/methacrylic acid), LUVIQUAT HM-552 (polyquaternium-16), LUVIQUAT HOLD (polyquaternium-16), LUVISKOL K30 (PVP) LUVISKOL K90 (PVP), LUVISKOL VA 64 (PVPNA copolymer) LUVISKOL VA73W (PVPNA copolymer), LUVISKOL VA, LUVISET PUR (Polyurethane-1), LUVISET Clear (VP/MethacrylamideNinyl Imidazole Copolymer), LUVIFLEX SOFT (Acrylates Copolymer), ULTRAHOLD 8 (Acrylates/Acrylamide Copolymer), LUVISKOL Plus (Polyvinylcaprolactam), LUVIFLEX Silk (PEG/PPG-25/25 Dimethicone/Acrylates Copolymer); from Amerchol, AMERHOLD DR-25 (acrylic acid/methacrylic acid/acrylates/methacrylates); from Rohm&Haas, ACUDYNE 258 (acrylic acid/methacrylic acid/acrylates/methacrylates/hydroxyl ester acrylates from Mitsubishi and distributed by Clariant, DIAFORMER Z-301, DIAFORMER Z-SM, and DIAFORMER Z-400 (methacryloyl ethyl betaine/acrylates copolymer), ACUDYNE 180 (Acrylates/Hydroxyesters Acrylates Copolymer), ACUDYNE SCP (Ethylenecarboxyamide/AMPSA/Methacrylates Copolymer), and the ACCULYN rheological modifiers; from ONDEO Nalco, FIXOMER A-30 and FIXOMER N-28 (INCI names: methacrylic acid/sodium acrylamidomethyl propane sulfonate copolymer); from Noveon, FIXATE G-100 (AMP-Acrylates/Allyl Methacrylate Copolymer), FIXATE PLUS (Polyacrylates-X), CARBOPOL Ultrez 10 (Carbomer), CARBOPOL Ultrez 20 (Acrylates/C10-30 Alkyl Acrylates Copolymer), AVALURE AC series (Acrylates Copolymer), AVALURE UR series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymer that is polar solvent soluble or that can be made soluble through neutralization with the appropriate base.

In certain embodiments, the personal care formulation is essentially free of additional moisturizers, humectants, and/or emollients. As used herein the term "essentially free of," with respect to a particular ingredients, refers to the particular ingredient being present in a concentration less than is necessary for the ingredient to be effective to provide the benefit or property for which it otherwise would be used, for example, about 0.5 wt % or less, or about 0.1 wt % or less, or about 0.05 wt % or less (based on the total weight of the personal care composition). In some other embodiments, the personal care formulation is essentially free of glycerol, hydroxyethyl urea, sodium lactate, and/or sodium pyrrolidone carboxylate (sodium PCA). In other embodiments, the personal care composition is essentially free of glycerol. In some other embodiments, the personal care composition is essentially free of panthenol (provitamin $B_5$).

Personal care formulations include, without limitation, lotions, creams (including for the face and body), serums, rinse-off body lotions, moisturizing cleansers, soaps, anti-aging products, nourishing creams and lotions, firming and toning products, shaving creams, depilatories, deodorants, color cosmetics foundations, makeups, lipsticks, sunscreens, suntan lotions, after-sun products, personal care wipes, baby care products, bath and shower products, hair shampoo, hair leave-in conditioner, hair rinse-off conditioner, hair gel, hair lotion, hair cream, mousse, hair spray, hair dyes, hair permanent wave, hair anti-frizz, and hair volumizing products.

In one embodiment, the personal care formulations of the disclosure comprise one or more cosmetically acceptable additives that are selected from thickeners, surfactants, emulsifiers, or combinations thereof. Such additives can be present in an amount of 0.1 or more % by weight of the personal care composition. In some other embodiments, one or more thickeners, surfactants, emulsifier, or combinations thereof is present from about 0.1% to about 5%, or about 0.1% to about 1%, or about 0.1% to about 0.5%, or about 0.5% to about 5%, or about 0.5% to about 1%, or about 1% to about 5%, or about 1% to about 10%, by weight of the personal care composition.

In one embodiment, the personal care formulations of the disclosure comprise one or more thickeners and one or more emulsifiers, each present in at least 0.1 or more % by weight of the personal care composition. In some other embodiments, each thickener and each emulsifier is independently present from about 0.1% to about 5%, or about 0.1% to about 1%, or about 0.1% to about 0.5%, or about 0.5% to about 5%, or about 0.5% to about 1%, or about 1% to about 5%, or about 1% to about 10%, by weight of the personal care composition.

In an exemplary embodiment, the personal care formulation comprises from about 1 wt % to about 7 wt % of compound of formula (I), about 0.1 wt % to about 1 wt % of a thickener, about 0.1 wt % to about 1 wt % of an emulsifier, and about 0.1 wt % to about 1 wt % of a preservative, based on the total weight of the personal care formulation.

In another exemplary embodiment, the personal care formulation comprises from about 4.5 wt % to about 5.5 wt % of compound of formula (I), about 0.4 wt % to about 0.6 wt % of a thickener, about 0.4 wt % to about 0.6 wt % of an emulsifier, and about 0.4 wt % to about 0.6 wt % of a preservative, based on the total weight of the personal care formulation.

In another aspect, the disclosure provides a kit comprising a container (e.g., a tube or jar) containing a formulation according to the invention and instructions for application of the formulation to the skin or hair for enhancing moisturization of the skin or hair, wherein the instructions are printed on the container, on the packaging of the container, or on a document included with the container.

In another aspect, the disclosure provides a method of moisturizing skin or hair, the method comprising applying an effective moisturizing amount of a personal care formulation of the disclosure to the skin or hair, respectively.

Definitions

The following terms and expressions used have the indicated meanings.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an," and "the" include plural referents unless the context clearly dictates otherwise.

As used herein, the term "about" refers to the given value ±10% of the value.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All percentages, ratios and proportions herein are by weight, unless otherwise specified. A weight percent (weight %, also as wt %) of a component, unless specifically stated to the contrary, is based on the total weight of the composition in which the component is included (e.g., on the total amount of the compositions). All mol % values are based on the moles of the active compounds.

As used herein, the term "alkyl" refers to a group comprised of one to six, unless otherwise noted, saturated carbon atoms connected in a linear or branched configuration. Examples of linear alkyl groups include methyl, ethyl, n-propyl, n-butyl, n-pentyl, and n-hexyl. Examples of branched alkyl groups include iso-propyl (1-methylethyl), tert-butyl (1,1-dimethylethyl), iso-butyl (2-methylpropyl), sec-butyl (1-methylpropyl), iso-pentyl (2-methylbutyl), neo-pentyl (2,2-dimethylpropyl), iso-hexyl (2-methylpentyl, 3-methylpentyl, and 2,3-dimethylbutyl), and neohexyl (2,2-dimethylbutyl).

As used herein, the term "cosmetically acceptable" means suitable for use in contact with the skin or hair of most humans and most members of lower animal species without undue toxicity, incompatibility, instability, irritation, allergic response, and the like.

EXAMPLES

The methods of the disclosure are illustrated further by the following examples, which are not to be construed as limiting the disclosure in scope or spirit to the specific procedures and in them.

Example 1: Preparation of Diglycolamine (DGA) Acetamide

A mixture of 42.06 g (0.4 mol) 2-(2-aminoethoxy)ethanol, 70.49 g (0.8 mol) of ethyl acetate, and 0.33 g phosphorous acid was refluxed in a 250 ml round bottom flask immersed in an oil bath under $N_2$ atmosphere. The mixture was refluxed until the reaction showed no further increase in the amide carbonyl peak (due to product) at 1646 cm$^{-1}$ wavenumber as monitored by FTIR (using a single-bounce ATR accessory with ZnSe crystal and DTGS detector with a Nicolet iS10 spectrometer). The excess ethyl acetate and the ethanol byproduct were then distilled off through downward distillation. Fresh ethyl acetate (35.24 g, 0.4 mol) was then added to the reaction mixture and the refluxing was continued until no further increase in the product formation was seen in the amide carbonyl peak at 1646 cm$^{-1}$ as monitored by FTIR. This process of stripping of excess ethyl acetate/ethanol and adding fresh ethyl acetate was repeated until the FTIR showed it to be the desired product no further increase in the amide carbonyl peak at 1646 cm$^{-1}$, indicating that the reaction of 2-(2-aminoethoxy)ethanol had gone to completion.

Example 2: Dynamic Vapor Sorption Analysis

Dynamic Vapor Sorption (DVS) technique was used to measure the moisture intake of a specific compound at certain humidity level. A DVS Intrinsic instrument manufactured by Surface Measurement Systems UK Ltd. (London, United Kingdom) was used to measure DVS. The following measurement procedure was used to determine the water vapor absorption of a specific compound.

A uniform aqueous solution of a specific, target compound was made at 50% concentration. About 1.2 to 1.6 mg of the prepared aqueous solution was added to DVS instrument at zero tare balance. The temperature was then set at 25° C., and the measurement was performed at various humidity levels. The first measurement was performed at a humidity of 90% to ensure that the sample absorbs the highest level of water in order to minimize the mass transfer barrier during the evaporation process. The typical humidity measurements were then taken at 50%, 40%, 30%, 20%, 10%, and 0% humidity. The dynamics of water absorption was determined by the weight change per minute. If weight change per minute was less than 0.005% of the sample weight, it was deemed that water absorption had reached the equilibrium point. The equilibrium weight at 0% humidity is the sample weight by itself. Thus, the percentage of equilibrium water absorption at various humidity levels was calculated.

Using the above procedure, DVS was used to evaluate water absorption for DGA Acetamide as compared to hydroxyethyl urea and glycerol at different humidity levels. The results are shown in Table 1.

TABLE 1

DVS measurement of water absorption by humectants at different humidity levels

| | Percentage of water absorbed based on weight of the tested compound (%) | | | | |
| --- | --- | --- | --- | --- | --- |
| Humectant | 10% rel. humidity | 20% rel. humidity | 30% rel. humidity | 40% rel. humidity | 50% rel. humidity |
| Hydroxyethyl urea | 2.4 | 5.4 | 9.2 | 14.1 | 19.7 |
| DGA acetamide | 2.6 | 5.9 | 9.9 | 15.3 | 26.9 |
| Glycerol | 4.6 | 8.6 | 15.9 | 23.3 | 27.7 |

The data demonstrate that DGA Acetamide shows water absorption capability on par with that for hydroxyethyl urea at relative humidity levels of 10%, 20% 30%, and 40%, and on par with glycerol at 50% relative humidity.

Example 3: Corneometer Analysis

Preparation of Gel Formulation

To prepare a gel formulation, deionized water was added to a 4 oz. tall jar that was set up for mixing using an overhead mixer and a jiffy blade. The water was then mixed at a speed that created a good vortex that nearly reached the bottom of the jar (e.g., about 700 rpm). To this, Carbopol® 940 (cross-linked polyacrylate polymer available from Lubrizol, Wickliffe, Ohio) was slowly added and mixed for at least 15 minutes until homogeneous. Triethanolamine (TEA) was then added and the mixing speed was adjusted overhead to about 200 rpm and continued mixing for about 10 minutes (e.g., product viscosity increased). To this mixture, 5 wt % of the sample compound in its pure form (or hydroxyethyl urea or glycerol control) was added followed by 0.5 wt % Glydant™ Plus™ (a preservative available from Lonza, Basel, Switzerland) and the remaining, balance water. Mixing was continued at 200 rpm for about 15-20 minutes. The mixture was then removed from the mixer and the final pH was measured. Prior to analysis, samples were centrifuged at 2000 rpm for 15 minutes to remove suspended air pockets from gel formula. The final gel formulation concentration is provided in Table 2.

TABLE 2

Formulations for Corneometer Studies

| Formulation ingredients | DGA Acetamide formulation | Glycerol formulation | Water formulation (as control) |
| --- | --- | --- | --- |
| Deionized water | 93.5 | 93.5 | 98.5 |
| DGA Acetamide | 5.0 | — | — |
| Glycerol | — | 5.0 | — |
| Glydant ™ Plus ™ Liquid | 0.5 | 0.5 | 0.5 |
| Carbopol ® 940 | 0.5 | 0.5 | 0.5 |
| TEA | 0.5 | 0.5 | 0.5 |

Corneometer Measurement

Corneometer measurements were taken on eight subjects to whose skin the gel samples of Table 2 had been applied. About 30 µl of the gel formulation containing the sample compound was applied once (e.g., in a single application with no additional re-applications) in a circle with diameter of about 3 cm on the inner forearm of each panelist. Moisture levels were measured using a Corneometer® CM 825 (available from CK Industries) prior to and at various time intervals after the sample application at a temperature of 22° C. and relative humidity of 50%, wherein the corneometer values recorded are the difference between the corneometer reading at a given time and the initial corneometer reading at 0 hours, which is set at zero.

Results

FIG. 1 shows the average of the corneometer readings for the eight panelists for each of the gel formulations tested over a period of 24 hours The data show that DGA acetamide was superior to the control formulation over the entire time range tested. DGA acetamide showed humectance performance similar to glycerol over 0-6 hours, and the same as glycerol at 24 hours. This excellent humectance performance is provided without the stickiness, tackiness or other undesirable tactile qualities usually associated with glycerol-based personal care products.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A personal care formulation comprising a compound of formula:

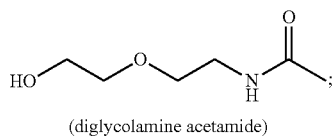

(diglycolamine acetamide)

at least one additive selected from the group consisting of sunscreen active agents, antiperspirant active agents, anti-acne agents, anti-dandruff agents, emollient agents, and combinations thereof; and
a cosmetically acceptable vehicle;
wherein the personal care formulation does not contain a polyol other than optionally glycerol.

2. The personal care formulation of claim 1, which further comprises at least one further additive selected from the group consisting of vitamins, botanical extracts, preservatives, exfoliants, film formers, propellants, UV filters, tanning accelerators, and hair fixatives.

3. The personal care formulation of claim 1, which further comprises at least one further additive selected from the group consisting of vitamins, botanical extracts, exfoliants, film formers, UV filters, tanning accelerators, and hair fixatives.

4. The personal care formulation of claim 1, wherein the diglycolamine acetamide is present in about 2% to about 7% by weight of the personal care formulation.

5. The personal care formulation of claim 1, comprising a thickener and an emulsifier, each present in at least 0.1% by weight of the personal care formulation.

6. The personal care formulation of claim 1, which excludes one or more additional humectants, moisturizers, emollients, or combinations thereof.

7. The personal care formulation of claim 1, which is a skin care formulation or a hair care formulation.

8. The personal care formulation of claim 1, which is selected from the group consisting of lotions, creams, serums, rinse-off body lotions, moisturizing cleansers, soaps, anti-aging products, nourishing creams and lotions, firming and toning products, shaving creams, depilatories, deodorants, color cosmetics foundations, makeups, lipsticks, sunscreens, suntan lotions, after-sun products, personal care wipes, baby care products, and bath and shower products, shampoo, leave-in conditioner, rinse-off conditioner, hair gel, hair lotion, hair cream, mousse, and hair spray.

9. A container containing a personal care formulation of claim 1 and instructions for application of the formulation to the skin or hair for enhancing moisturization of the skin or hair, wherein the instructions are printed on the container, on the packaging of the container, or on a document included with the container.

10. The personal care formulation of claim 8, which is selected from the group consisting of lotions, creams, serums, rinse-off body lotions, moisturizing cleansers, soaps, anti-aging products, and nourishing creams and lotions.

11. The personal care formulation of claim 8, which is selected from the group consisting of shampoo, leave-in conditioner, rinse-off conditioner, hair gel, hair lotion, hair cream, mousse, and hair spray.

12. A method of moisturizing skin or hair in a subject, the method comprising applying an effective moisturizing amount of a personal care formulation of claim 1 to the skin or hair of the subject.

13. A personal care formulation comprising a compound of formula:

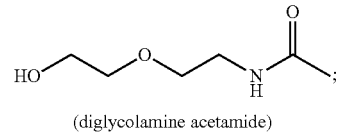

(diglycolamine acetamide)

at least one additive selected from the group consisting of sunscreen active agents, antiperspirant active agents, anti-acne agents, anti-dandruff agents, and combinations thereof; and
a cosmetically acceptable vehicle.

14. A method of moisturizing skin or hair in a subject, the method comprising applying an effective moisturizing amount of a personal care formulation of claim 13 to the skin or hair of the subject.

* * * * *